United States Patent
Bigi et al.

(10) Patent No.: US 10,239,900 B2
(45) Date of Patent: Mar. 26, 2019

(54) PROCESSES FOR PRODUCING ORGANOPHOSPHOROUS COMPOUNDS

(71) Applicant: Dow Technology Investments LLC, Midland, MI (US)

(72) Inventors: Marinus A. Bigi, Freeport, TX (US); Michael A. Brammer, Freeport, TX (US); Glenn A. Miller, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/752,407

(22) PCT Filed: Sep. 7, 2016

(86) PCT No.: PCT/US2016/050481
§ 371 (c)(1),
(2) Date: Feb. 13, 2018

(87) PCT Pub. No.: WO2017/058475
PCT Pub. Date: Apr. 6, 2017

(65) Prior Publication Data
US 2019/0002485 A1    Jan. 3, 2019

Related U.S. Application Data

(60) Provisional application No. 62/234,938, filed on Sep. 30, 2015.

(51) Int. Cl.
*C07F 9/6574* (2006.01)
*B01D 9/00* (2006.01)

(52) U.S. Cl.
CPC ........ *C07F 9/65746* (2013.01); *B01D 9/0054* (2013.01)

(58) Field of Classification Search
CPC .................. C07F 9/65746; B01D 9/0054
USPC ........................................................ 558/78
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,116,926 A | 9/1978 | York |
| 4,567,302 A | 1/1986 | Sivaramakrishnan |
| 4,567,306 A | 1/1986 | Dennis et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,312,996 A | 5/1994 | Packett |
| 5,323,996 A | 6/1994 | Rendall |
| 5,364,950 A | 11/1994 | Babin et al. |
| 5,391,801 A | 2/1995 | Sato et al. |
| 5,527,950 A | 6/1996 | Hansen et al. |
| 5,688,986 A | 11/1997 | Tam et al. |
| 7,767,861 B2 | 8/2010 | Ortmann et al. |
| 8,461,394 B2 | 6/2013 | Lueken et al. |
| 2011/0130595 A1 | 6/2011 | Lueken et al. |
| 2013/0225849 A1 | 8/2013 | Berens et al. |
| 2014/0288322 A1 | 9/2014 | Miller et al. |
| 2017/0240578 A1 | 8/2017 | Phillips et al. |

FOREIGN PATENT DOCUMENTS

| | | | |
|---|---|---|---|
| CN | 101684130 A | 3/2010 | |
| CN | 102432638 A | 5/2012 | |
| EP | 0213639 A2 | 3/1987 | |
| JP | 09-077713 | 3/1997 | |
| WO | 97/20797 A1 | 6/1997 | |
| WO | WO-2013066712 A1 * | 5/2013 | .......... C07F 9/65746 |
| WO | 2013098370 | 7/2013 | |

OTHER PUBLICATIONS

PCT/US2016/050481, International Search Report and Written Opinion of the International Searching Authority, dated Nov. 29, 2016.
PCT/US2016/050481, International Preliminary Report on Patentability, dated Apr. 3, 2018.

* cited by examiner

*Primary Examiner* — Kristin A Vajda

(57) ABSTRACT

The present invention relates to processes for producing organophosporous compositions having low acid content as well as processes for reprocessing partially degraded organophosporous compositions that contain high levels of phosphorous acid. In one embodiment, a process comprises: (a) receiving a solid organophosphite compound that has been recrystallized or triturated, wherein the solid organophosphite compound comprises phosphorous acid; (b) dissolving the solid organophosphite compound in a an aromatic hydrocarbon solvent in the absence of water and free amine, wherein the hydrocarbon solvent comprises an aromatic hydrocarbon, a saturated aliphatic hydrocarbon, or a mixture thereof; and (c) removing undissolved phosphorous acid from the solution, wherein the acid content of the organophosphite following step (c) is 30 ppm or less.

15 Claims, No Drawings

PROCESSES FOR PRODUCING ORGANOPHOSPHOROUS COMPOUNDS

FIELD

The disclosure in general relates to organophosphorous compositions that are stable during long-term storage and to processes for producing organophosporous compositions having low acid content as well as processes for reprocessing partially degraded organophosporous compositions that contain high levels of phosphorous acid.

INTRODUCTION

Organophosphites and polyorganophosphites have been used for a variety of applications including as preservatives (e.g., antioxidants) for plastic materials and as ligands for homogeneous catalysis. However, maintaining the stability of phosphite ligands can be problematic. To be effective, the ligand and related catalyst must be stable under reaction conditions. The stability of the ligand can be negatively impacted by impurities, especially those that accumulate in the ligand during storage.

For example, acidic byproducts are known to cause hydrolytic degradation of phosphites, and thus require particular attention. A number of schemes have been developed to mitigate acids such as water extraction and/or the use of excess amines (e.g., triethylamine or pyridine as in U.S. Pat. No. 5,235,113). For example, in U.S. Pat. No. 5,235,113, the ammonium hydrochloride salt is extracted into water and then the organic phase containing the crude ligand product is dried with $MgSO_4$, filtered before evaporating to a residue, and recrystallized.

U.S. Patent Pub. No. 2013/0225849 discloses the use of trace amounts of sodium methoxide as an additive in a washing step during the purification phase of the ligand manufacturing process to address the issue of acidic impurities. However, the presence of residual strong base is not suitable in many catalytic processes, such as hydroformylation, hydrocyanation or hydrogenation.

There remains a need for a simple process to produce phosphites of exceptionally low acid content to assure long-term storage stability, as well as a facile means of reprocessing partially degraded phosphites that contain high levels of phosphorous acid.

SUMMARY

We have found that the long-term storage stability of organophosphites is greatly influenced by the phosphorous acid content of the material at the time it is packaged, and that manufacturing processes that employ water or water/amine extraction to remove acidic impurities often leave significant amounts of residual phosphorous acid in the final product. Surprisingly, it has been discovered that embodiments of the present invention reduce the phosphorous acid content of organophosphites to extremely low levels, and moreover, that the organophosphite thus produced is exceptionally stable during long-term storage. Embodiments of the present invention may also be utilized to remove phosphorous acid from phosphites that have partially degraded over time due to improper preparation, packaging or storage.

In one embodiment, a process of the present invention comprises (a) receiving a solid organophosphite compound that has been recrystallized or triturated, wherein the solid organophosphite compound comprises phosphorous acid; (b) dissolving the solid organophosphite compound in a hydrocarbon solvent, wherein the hydrocarbon solvent comprises an aromatic hydrocarbon, a saturated aliphatic hydrocarbon, or a mixture thereof; and (c) removing undissolved phosphorous acid from the solution, wherein the acid content of the organophosphite following step (c) is 30 ppm or less.

DETAILED DESCRIPTION

In one embodiment, a process of the present invention comprises receiving a solid organophosphite compound that has been recrystallized or triturated, wherein the solid organophosphite compound comprises phosphorous acid, dissolving the solid organophosphite compound in a hydrocarbon solvent, wherein the hydrocarbon solvent comprises an aromatic hydrocarbon, a saturated aliphatic hydrocarbon, or a mixture thereof, and removing undissolved phosphorous acid from the solution. The organophosphite thus obtained has an acid content (e.g., a phosphorous acid content) of 30 ppm or less in some embodiments, 10 ppm or less in some embodiments, and 5 ppm or less in some embodiments. In some embodiments, the undissolved phosphorous acid is removed by filtration, while in other embodiments, the undissolved phosphorous acid is removed by centrifugation. In some embodiments, the solid organophosphite compound is dissolved in the hydrocarbon solvent in the absence of water and free amine.

In some embodiments, the process further comprises (e.g., after removal of the undissolved phosphorous acid) concentrating the organophosphite in hydrocarbon solution, combining the concentrated organophosphite in hydrocarbon solution with an anti-solvent, and collecting the resulting solids. In some such embodiments, the organophosphite in hydrocarbon solution is concentrated to a residual hydrocarbon content of 50% by weight or less. In some embodiments, the process further comprises storing the resulting solids for at least 30 days, wherein the stored resulting solids comprise 25 ppm or less phosphorous acid after 30 days. In some embodiments where anti-solvent is combined with the concentrated organophosphite, the anti-solvent can be added to the concentrated organophosphite in hydrocarbon solution. Examples of anti-solvent that can be used in some such embodiments include isopropanol and t-butanol.

In some embodiments, after the purified organophosphite compound is collected according to some embodiments of the present invention, 0.05 to 13 acid-neutralizing equivalents per 100 moles ligand of an acid-scavenger is added to the product.

The organophosphite compound, in some embodiments, comprises at least one of the following:

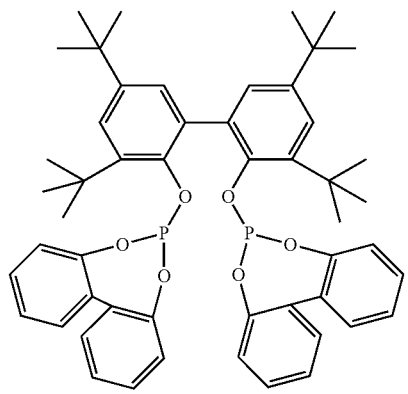

-continued

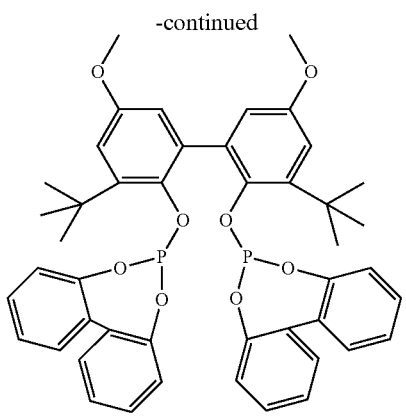

The organophosphite collected according to some embodiments of the present invention can be provided to a hydroformylation process. In some embodiments, the solid organophosphite compound comprising phosphorous acid that is provided at the beginning of some embodiments of processes of the present invention has been stored for at least 30 days.

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For example, unless otherwise stated to the contrary, when relative amounts are provided as "parts per million", "ppm", "parts per billion", "ppb", or "parts" such amounts are on the basis of mass. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

Unless stated to the contrary, or implicit from the context all procedures described herein should be conducted under air-free conditions. Any suitable means to achieve air-free conditions (e.g. purging of systems with nitrogen or argon, etc.) may be employed.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about."

In such instances the term "about" refers to numerical ranges and/or numerical values that are substantially the same as those recited herein.

As used herein, the term "hydroformylation" is contemplated to include, but is not limited to, all processes that involve converting one or more olefinic compounds to one or more aldehydes using carbon monoxide, hydrogen, and a catalyst comprised of a transition metal and an organophosphite ligand.

For purposes of this invention, the term "aromatic hydrocarbon" is contemplated to include all permissible compounds comprised of carbon and hydrogen atoms, and containing at least one benzene moiety. Such benzene moieties may be substituted or unsubstituted. As used herein, the term "aromatic hydrocarbon" does not include nitrogen, sulfur, and oxygen moieties. Examples of aromatic hydrocarbons include toluene, xylenes, and the like. Suitable compounds will have a dielectric constant at or below 5 $\varepsilon_r(\omega)$ (at 20° C.).

For purposes of this invention, the term "saturated aliphatic hydrocarbon" is contemplated to include alkanes such as hexane, heptane, cyclohexane, cycloheptane, and the like.

For purposes of this invention, the term "hydrocarbon solvent" is contemplated to include aromatic hydrocarbons and mixtures comprising aromatic hydrocarbons and saturated aliphatic hydrocarbons. The hydrocarbon solvent is employed to provide dissolution of the organophosphite.

As used herein, the term "anti-solvent" is contemplated to comprise polar solvents and mixtures thereof that are incapable of dissolving appreciable amounts of the solid hydrolyzable organophosphite. Suitable anti-solvents have dielectric constants above 15 $\varepsilon_r(\omega)$ (at 20° C.) yet are still miscible with the hydrocarbon solvent. Examples include acetonitrile and alcohols, such as isopropanol, tertiary butanol, and the like. The anti-solvent is employed to facilitate crystallization of the organophosphite or as a trituration solvent.

As used herein, the term "trituration" describes a process wherein organophosphite or a concentrate comprising organophosphite and hydrocarbon solvent is combined with an anti-solvent and mixed thoroughly. In contrast to a recrystallization, a trituration does not involve appreciable dissolution of the organophosphite, but rather comprises slurrying the organophosphite in an anti-solvent. The trituration may be conducted using varying proportions of anti-solvent relative to organophosphite and at different temperatures.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, in which the number of carbons can range from 1 to 20 or more, preferably from 1 to 12, as well as hydroxyl and halogen. The permissible substituents can be one or more and the same or different for appropriate organic compounds. This invention is not intended to be limited in any manner by the permissible substituents of organic compounds.

Hydrolyzable organophosphorous ligands are trivalent phosphorous compounds that contain at least one P—Z bond wherein Z is oxygen, nitrogen, chlorine, fluorine or bromine. Organophosphites are a type of hydrolyzable organophosphorous ligand that is a trivalent phosphorous compound that contains at least one P—Z bond wherein Z is oxygen. Examples of hydrolyzable organophosphorous ligands include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligand may include chelate structures and/or may contain multiple P—Z moieties such as polyphosphites, polyphosphoramidites, etc. and mixed P—Z moieties such as phosphite-phosphoramidites, flurophosphite-phosphites, and the like. Examples of phosphite ligands include mono-organophosphite, diorganophosphite, triorganophosphite and organopolyphosphite compounds. Such organophosphorous compounds and methods for their preparation are well known in the art. Mixtures of hydrolyzable organophosphorous ligands can be employed.

Representative monoorganophosphites may include those having the formula:

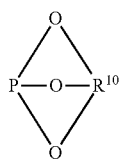

wherein $R^{10}$ m represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306.

Representative diorganophosphites may include those having the formula:

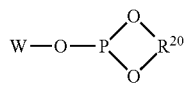

wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, and cycloalkylene radicals. The more preferred divalent acyclic radicals are the divalent alkylene radicals such as disclosed more fully, for example, in U.S. Pat. Nos. 3,415,906 and 4,567,302. Illustrative divalent aromatic radicals include, for example, arylene, bisarylene, arylene-alkylene, arylene-alkylene-arylene, arylene-oxy-arylene, arylene-S-arylene, arylene-S-alkylene, and the like. More preferably $R^{20}$ is a divalent aromatic radical such as disclosed more fully in, for example, U.S. Pat. Nos. 4,599,206, 4,717,775, and 4,835,299.

Representative of a more preferred class of diorganophosphites are those of the formula:

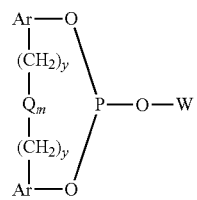

wherein W is as defined above, each Ar is the same or different and represents a substituted or unsubstituted aryl radical, each y is the same or different and is a value of 0 or 1, Q represents a divalent bridging group selected from —C($R^{33}$)$_2$—, —O—, —S—, Si($R^{35}$)$_2$ and —O—, wherein each $R^{33}$ is the same or different and represents hydrogen, an alkyl radical having from 1 to 12 carbon atoms, phenyl, tolyl, and anisyl, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)phenylphosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

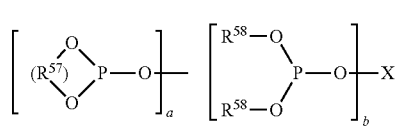

wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616; 5,364,950; and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

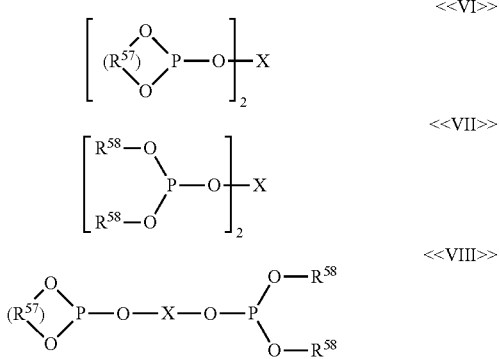

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite compounds of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^{35})_2$— where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —$Si(R^{35})_3$; phosphine radicals such as -aryl-$P(R^{15})_2$; alkoxy radicals such as —$OR^{15}$; phosphonyl radicals such as —$P(O)(R^{15})$ 2, as well as halo, trifluoromethyl, and the like, wherein each $R^{15}$ radical individually represents the same or different monovalent hydrocarbon radical having from 1 to 18 carbon atoms (e.g., alkyl, aryl, aralkyl, alkaryl and cyclohexyl radicals). It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl, and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$O(CH_2CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; arylphosphine radicals such as —$P(C_6H_5)_2$ and the like; sulfinyl radicals such as —$S(O)CH_3$ and the like; sulfidyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of such organophosphite compounds include the following: 2-t-butyl-4-methoxyphenyl(3,3'-di-t-butyl-5,5'-dimethoxy-1,1'-biphenyl-2,2'-diyl) phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1'-biphenyl)]-2,4-pentyldiphosphite, (2R,4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl] methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

Hydrolyzable organophosphorous ligands and general methods for their manufacture are well-known to those skilled in the art. In general, hydrolyzable organophosphorous ligands are produced by the reaction of $PCl_3$ with H—Z compounds, where Z is as defined herein, in the presence of a base (usually an amine or amine resin). The actual synthetic route to the crude hydrolyzable organophosphorous ligand prior to the steps described herein is not a critical feature of the invention.

In one aspect, the invention comprises a solid organophosphite composition that is substantially free of amine and water. It has surprisingly been discovered that the presence of amines, which when combined with phosphorous acid will form salts that the skilled person would expect to be lower in solubility in hydrocarbon solvent than the free acid, actually reduces the ability to remove phosphorous acid by filtration. Thus recrystallizing or triturating the crude hydrolyzable organophosphite ligand in a suitable solvent at least once prior to the process of the invention is required to assure that the organophosphite employed in the invention is substantially free of water and amine Solvents known to be suitable for the initial recrystallization of organophosphite ligands may be found for example in WO2013066712 and WO2013098370. Examples of preferred recrystallization solvents include ethyl acetate, isopropyl acetate, propyl acetate, toluene and acetone. Solvents suitable for trituration comprise anti-solvents, such as acetonitrile and alcohols, including isopropanol, t-butanol and the like. The term "substantially free of water and free amine" is contemplated to comprise a solid organophosphite composition that has been recrystallized or triturated at least once in a suitable solvent.

The hydrocarbon solvent should be capable of dissolving the organophosphorous ligand and will typically have a dielectric constant less than 5 $\varepsilon_r(\omega)$. Examples of preferred aromatic hydrocarbons employed for the hydrocarbon solvent include toluene, xylenes, benzene, ethylbenzene and the like. The amount of hydrocarbon solvent employed is not critical, but should be sufficient to dissolve substantially all of the ligand at the filtration temperature. Advantageously, the filtration temperature is from 20° C. up to the boiling point of the solvent. In one aspect, the invention comprises dissolving a solid hydrolyzable organophosphite ligand in a hydrocarbon solvent in the absence of water and free amine, and then separating the solution from insoluble phosphorous acid such that the resulting filtrate contains less than 30 ppm phosphorus acid, based on the mass of organophosphite. The separation can be done by filtration or centrifugation. This separation can be achieved by filtering the solution through a filter whose effective porosity is ≤1 micron. It has surprisingly been discovered that the solubility of phosphorous acid in a matrix comprised substantially of a hydrocarbon solvent and dissolved organophosphite is exceptionally low, and that within such a matrix, phosphorous acid exists in a form amenable to separation by filtration.

The filtration should employ as fine a filter as practical but at a minimum should be performed with an effective porosity of less than or equal to 1 micron. Filter aids and body aids (celites, etc.) may be employed to enhance filter efficiency. It has been found that when the majority of the particles above 1 micron mean diameter have been removed, the resulting solution will exhibit phosphorous acid content below 30 ppm. The filtration efficiency can be monitored by observation of the mean particle size by known techniques such as laser particle size determination or by measuring the concentration of the phosphorous acid in solution. The filtration temperature is not critical, but in general should be as low as practical to minimize the solubility of impurities (e.g., below 40° C.). If necessary, elevated temperatures may be employed to speed or maintain the dissolution of the solid organophosphite. Filtration can be accomplished using multiple filters in series, passing the solution through the same filter multiple times, or other techniques known to those of skill in the art so as to achieve a phosphorous acid content below 30 ppm.

An alternative to filtration can be centrifugation employing equipment such as solid bowl decanters, disc stack centrifuges, centrifugal filters, etc. Filtration and centrifugation can also be done in series.

In one aspect of the invention, the acid-free filtrate is concentrated by removing a portion of the hydrocarbon solvent. Various means of facilitating solvent removal via vacuum, or under a flow of inert gas at elevated temperatures are known to the skilled person. A preferred method is to place the solution under vacuum at moderate temperature. In general it is desirable to remove as much of the hydrocarbon solvent as practical. The solvent thus removed may be recycled in the case of continuous operation.

In one embodiment, the concentrated solution comprising organophosphite and hydrocarbon solvent is transferred to a second vessel containing an anti-solvent. In such an embodiment, the volume of hydrocarbon solvent should not be reduced beyond the solubility limit of the organophosphite. In other words, effectively transferring the concentrated solution comprising the organophosphite and hydrocarbon solvent to a second vessel, requires that the organophosphite remain in solution. The temperature at which the transfer takes place will, to a large degree, dictate the amount of hydrocarbon solvent that may be removed during the concentration step.

In a preferred embodiment, the hydrocarbon solvent is substantially removed to leave the concentrate comprising organophosphite and hydrocarbon solvent as a solid or slush. Although the amount of hydrocarbon solvent remaining in the concentrate is not critical, advantageously a mixture of approximately 50:50 by weight organophosphite and hydrocarbon solvent is achieved. In such an embodiment, an anti-solvent is transferred to the vessel containing the concentrate comprising the organophosphite and hydrocarbon solvent.

In one aspect the concentrate comprising the organophosphite and hydrocarbon solvent is combined and mixed with an anti-solvent. The volume of anti-solvent should be equal to or greater than the volume of the concentrate comprising the organophosphite and hydrocarbon solvent (e.g. at least 1 part of anti-solvent for every part of concentrate), and in some cases a large excess of anti-solvent may be employed. Once combined, the mixture may advantageously be heated with agitation to ≥65° C. for an hour or more to obtain a solid that will dry quickly as described in PCT Publication No. WO2013/066712. The resulting solid phosphite should then be collected (e.g. via filtration or centrifugation), washed with a portion of the anti-solvent and dried. The particular methods of such filtration, washing and drying are not critical, and exemplary methods have been described previously in PCT Publication No. WO2013066712.

The invention is also useful to reprocess partially degraded material that has generated phosphorous acid during storage. In this case, the phosphite is charged to a suitable vessel, dissolved in hydrocarbon solvent and separated as described above. The resulting low phosphorous acid solution is then concentrated, combined with the anti-solvent and processed as above.

Optionally an acid scavenger may be added which is a compound that serves to further increase the storage stability of the hydrolyzable organophosphorous ligand as described in PCT Application Serial No. PCT/US2015/026648). The optional acid scavenger is preferably added during the final step of the invention or is admixed with solid hydrolyzable organophosphorous ligand before or during packaging. When the optional acid scavenger is added to the antisolvent, the amount of acid scavenger is between 0.01 and 1 wt %, more preferably between 0.05 and 0.5 wt % of the total solution.

Some embodiments of the present invention will now be described in detail in the following Examples.

EXAMPLES

All parts and percentages in the following examples are by weight unless otherwise indicated. All manipulations are done in a $N_2$-glove box or via Schlenk techniques to exclude air and moisture unless otherwise indicated. Solid Ligand A or B is used in the following examples:

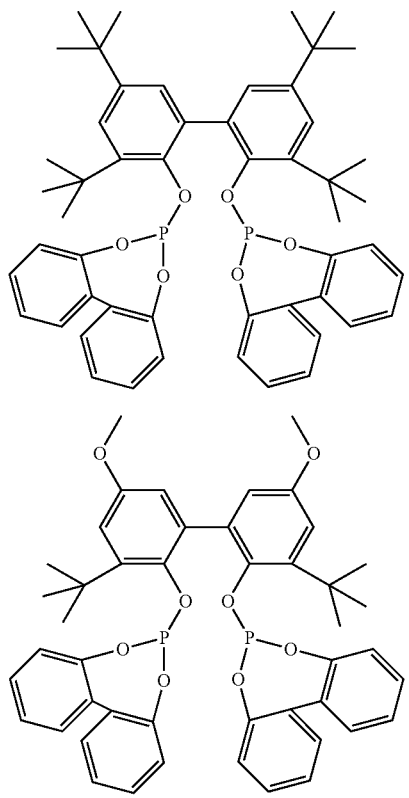

Ligand A

Ligand B

Phosphorous acid content of solid organophosphite is determined by ion chromatography (IC) using a Dionex ICS 2100 ion chromatograph with eluent generation and suppressed conductivity detection including a carbonate removal device. The chromatograph is fitted with an IonPac AG11-HC Guard Column and an IonPac AS11-HC Analytical Column. Data analysis is performed with Chromeleon 7.0 software. Unless otherwise indicated, samples are prepared by dissolution of the solid ligand (0.1 to 0.5 g) in toluene (5-10 mL) followed by extraction of the toluene solution with aqueous sodium hydroxide (0.004 M; 12-15 mL) or deionized water (8-15 mL). Acid content of toluene solutions are determined in like fashion. Phosphorous acid quantitation is reported as part per million by weight in the organophosphite. Samples containing very high levels of acid require additional dilution of the aqueous extract to stay within the calibration range. Unless otherwise indicated, Ligand A or B used herein is not crude material but has previously been purified via recrystallization as described, for example, in PCT Publication No. WO2013/066712.

Comparative Experiments A, B and C

Solid Ligand A (0.3 g) containing 9000-10,000 ppm phosphorous acid is weighed into each of three 20 mL glass vial and dissolved as indicated. Each solution is then filtered through a syringe filter of 0.20 micron porosity. The filtrates are extracted with water and the water layer is analyzed by IC. The results are summarized in Table 1.

TABLE 1

Filtration of Ligand A dissolved in various solvents and filtered through 0.2μ filters.

| Comparative Experiment | solvent | solvent (g) | dissolution/ filtration temperature (° C.) | Post-filtration phosphorous acid (ppm) |
|---|---|---|---|---|
| A | Ethyl acetate | 6.2 | 40 | 8454 |
| B | Benzyl ether | 7.8 | 22 | 8243 |
| C | Ethyl ether | 11.1 | 22 | 10200 |

Comparative Experiments A, B and C show that simply filtering a solution of organophosphite in ethyl acetate, benzyl ether or ethyl ether does not significantly lower phosphorous acid content.

Examples 1 and 2, Comparative Experiment D

Solid Ligand A (1.0 g) containing 2250 ppm phosphorous acid is weighed into 20 mL glass vials and dissolved in toluene (8.0 g) containing small amounts of pyridine at ambient temperature. The solutions are then filtered through syringe filters of 0.45 micron porosity, and the filtrates are extracted with water and the water layer is analyzed by IC. Each experiment is performed in duplicate, and the average values for each are summarized in Table 2.

TABLE 2

Filtration of Ligand A dissolved in toluene/pyridine.

| | pyridine (wt %) | post-filtration phosphorous acid (ppm) |
|---|---|---|
| Example 1 | 0.1 | 2.2 |
| Example 2 | 1.0 | 10.9 |
| Comparative Experiment D | 5.0 | 66.0 |

The results of Table 2 show a direct relationship between the amount of amine in solution and a reduction in phosphorous acid separation efficiency.

Comparative Experiment E

The following procedure is conducted on a commercial scale: 2,2'-Biphenol (250 parts) and pyridine (3.75 parts) are dissolved in toluene (1730 parts) and cooled to 0-5° C. Phosphorous trichloride (289 parts) is added and the slurry is slowly warmed to 34-35° C. and stirred for 18 hours. Excess phosphorous trichloride is removed by distillation (120° C., atmospheric pressure). The resulting solution is cooled to 0-5° C. and pyridine (314 parts) is added. A solution of 4,4,6,6-tetra-tert-butyl-2,2'-biphenol (274 parts) in toluene (1550 parts) is slowly added to the first solution with good stirring while maintaining the temperature below 5° C. The resulting slurry is warmed slowly to 35° C. for 12-18 hours until the reaction is complete. Water (1370 parts) is then added to dissolve the acid salts and the water layer is discarded. The resulting toluene layer is azeotropically dried, filtered through a 5 micron filter, and concentrated under vacuum to a residue which is then recrystallized from ethyl or propyl acetate. Trituration of the resulting solids with isopropanol then drying under vacuum gives Ligand A as a crystalline powder. Three different commercial lots prepared in this manner contain an average of 77 ppm phosphorous acid in the final product.

Comparative Experiment E demonstrates that significant levels of phosphorous acid are commonly present in Ligand A following synthesis.

Comparative Experiments F and G

Solid Ligand A (0.3 g) containing 1288 ppm phosphorous acid is weighed into 20 mL glass vials and dissolved in toluene (6.5 g) at ambient temperature and at 70° C. The solutions are filtered through 5.0μ syringe filters. The filtrates are extracted with water and the water layer is analyzed by IC. The results are summarized in Table 3.

TABLE 3

Filtration of Ligand A dissolved in toluene through a 5.0μ filter.

| Comparative Experiment | filtration temperature (° C.) | Post-filtration phosphorous acid (ppm) |
|---|---|---|
| F | 23 | 862.2 |
| G | 70 | 743.5 |

The results of Table 3 show that a single-pass filtration through a 5.0μ filter is not adequate.

Examples 3-5

Solid Ligand A (0.3 g) containing 1289 ppm phosphorous acid is weighed into 20 mL glass vials and dissolved in toluene (6.5 g) at ambient temperature. The solutions are filtered through syringe filters of varying porosity. The filtrates are extracted with water and the water layer is analyzed by IC. The results are summarized in Table 4.

TABLE 4

Filtration of Ligand A dissolved in toluene through varying porosity filters.

| Example | Filter (micron) | Post-filtration phosphorous acid (ppm) | % of phosphorous acid removed |
|---|---|---|---|
| 3 | 0.20 | 6.7 | 99.48 |
| 4 | 0.45 | 4.5 | 99.65 |
| 5 | 1.00 | 21.6 | 98.32 |

The examples clearly demonstrate a method to achieve a reduction in phosphorous acid content by filtration of a solution comprising an organophosphite and toluene with a low porosity filter.

Examples 6-8

The procedure of Examples 1-3 is repeated with the exception of heating the solutions to 70° C. immediately prior to filtration. The results are summarized in Table 5.

TABLE 5

Filtration of Ligand A dissolved in toluene through varying porosity filters at 70° C.

| Example | Filter (micron) | Post-filtration phosphorous acid (ppm) | % of phosphorous acid removed |
|---|---|---|---|
| 6 | 0.20 | 1.5 | 99.88 |
| 7 | 0.45 | 3.2 | 99.75 |
| 8 | 1.00 | 11.0 | 99.14 |

Examples 6-8 show that the temperature at which the filtration is conducted is not critical.

Example 9

Solid Ligand A (0.3 g) containing 8986 ppm phosphorous acid is weighed into a 20 mL glass vial and dissolved in 1:1 toluene:heptane (6.0 g) at 40° C. The solution is filtered through a 0.45μ syringe filter. The filtrate is extracted with water and the water layer is analyzed by IC. The phosphorous acid content of the Ligand A post-filtration is 29.2 ppm.

Examples 10-11

Solid Ligand A (0.2 g) containing 594 ppm phosphorous acid is weighed into 20 mL glass vials and dissolved in benzene or p-xylene (7.0 g) at ambient temperature. The solutions are filtered through 0.20μ syringe filters. The filtrates are extracted with water and the water layer analyzed by IC. The results are summarized in Table 6.

TABLE 6

Filtration of Ligand A dissolved in benzene or p-xylene through 0.20μ filters.

| Example | solvent | Post-filtration phosphorous acid (ppm) | % of phosphorous acid removed |
|---|---|---|---|
| 10 | benzene | 2.3 | 99.61 |
| 11 | p-xylene | 2.9 | 99.51 |

Examples 12-15

Solid Ligand A (0.3 g) containing 65.3 ppm phosphorous acid is weighed into 20 mL glass vials and dissolved in toluene (6.5 g) at ambient temperature. Celite (0.5 g of Celite 545; not acid washed) was added as indicated and the resulting slurries stirred for about 5 minutes. The slurries are then charged to syringes outfitted with a glass wool plug or filters as shown. The filtrates are extracted with water and analyzed by IC. The results are summarized in Table 7.

TABLE 7

Filtration of Ligand A using Celite 545.

| Example | Celite (g) | Filter | post-filtration phosphorous acid (ppm) | % of phosphorous acid removed |
|---|---|---|---|---|
| 12 | 0.5 | glass wool | 3.3 | 94.95 |
| 13 | 0.5 | 5.00 micron | 0.6 | 99.14 |
| 14 | 0.5 | 0.20 micron | 0.5 | 99.25 |
| 15 | 0 | 0.20 micron | 0.8 | 98.77 |

Experiments 12-15 show that Celite 545 enhances filtration capability (e.g. performance of the 5.00 micron filter is acceptable and comparable to the 0.20 micron filter). Moreover the data shows that good results may be achieved by simply depositing a slurry of Celite 545 on glass wool.

Examples 16-19

The procedure of Examples 10-13 is repeated, with the exception that the Ligand A employed contains 8986 ppm of phosphorous acid. The results are summarized in Table 8.

TABLE 8

Filtration of Ligand A with a high acid content using Celite 545.

| Example | Celite (g) | Filter | post-filtration phosphorous acid (ppm) | % of phosphorous acid removed |
|---|---|---|---|---|
| 16 | 0.5 | glass wool | 10.4 | 99.88 |
| 17 | 0.5 | 5.00 micron | 29.4 | 99.67 |
| 18 | 0.5 | 0.20 micron | 1.3 | 99.99 |
| 19 | 0 | 0.20 micron | 4.1 | 99.95 |

The examples of Table 8 again demonstrate the benefit of using Celite, and moreover show that the process of the invention is effective for organophosphites of extremely high acid content.

Example 20

Solid Ligand B (0.1 g) containing 6041 ppm phosphorous acid is weighed into a 20 mL glass vial and dissolved in toluene (8.8 g) at ambient temperature. Celite (1.0 g of Celite Standard Super-Cel) is added and the resulting slurry stirred for about 5 minutes. The slurry is then charged to a syringe outfitted with a 0.2µ filter; the filtrate is collected, extracted with water and the aqueous layer analyzed by IC. The acid content of the organophosphite is determined to be 3.4 ppm.

The results of Example 20 clearly show that the present invention is effective for Ligand B.

Example 21

Solid Ligand A (10.9 g) recrystallized from ethyl acetate and containing 41.5 ppm phosphorous acid is weighed into a 200 mL round bottom flask and dissolved in toluene (34.4 g) at ambient temperature. The resulting solution is filtered through a 0.2 micron syringe filter and the filtrate is then concentrated on a rotary evaporator until a slush containing 9.0 g of residual toluene is achieved. Isopropanol (100 mL) is added to the slush, and the mixture is triturated at 70° C. for about one hour. The solids are then collected, washed with isopropanol (30 mL) and dried in vacuo. The Ligand A thus obtained contains 0.7 ppm phosphorous acid (removal of 98.3% of the original phosphorous acid).

Comparative Experiment H and Examples 22-23

An accelerated storage test is conducted wherein the low-acid solid Ligand A prepared in Example 21 (6 g) and two additional samples of solid Ligand A containing varying amounts of phosphorous acid are charged to small glass jars, left uncapped, and lowered into a larger glass jar containing a small amount of water saturated with sodium chloride. The outermost jars are then capped and placed in a 40° C. oven. The relative humidity inside the jar is 75% (Journal of Research of the National Bureau of Standards—A. Physics and Chemistry Vol. 81 A, No. 1, January-February 1977).

The samples are removed periodically, mixed gently, and sampled for IC analysis. The results are summarized in Table 9.

TABLE 9

Relationship between acid content and stability for Ligand A.

| Example | Initial phosphorous (ppm) | phosphorous acid (ppm) After 3 days | phosphorous acid (ppm) After 8 days |
|---|---|---|---|
| Comp. Ex. H | 65.0 | 156.3 | 471.2 |
| 22 | 8.6 | 11.6 | 25.6 |
| 23 | 0.7 | 1.1 | 0.9 |

The results summarized in Table 9 clearly show that lowering the acid content of Ligand A enhances its storage stability under harsh conditions. Thus the current invention provides a means to produce organophosphites that will remain stable during long-term storage by producing a final product of exceptionally low acid content.

What is claimed is:

1. A process comprising: (a) receiving a solid organophosphite compound that has been recrystallized or triturated, wherein the solid organophosphite compound comprises phosphorous acid; (b) dissolving the solid organophosphite compound in a hydrocarbon solvent, wherein the hydrocarbon solvent comprises an aromatic hydrocarbon, a saturated aliphatic hydrocarbon, or a mixture thereof; and (c) removing undissolved phosphorous acid from the solution, wherein the acid content of the organophosphite following step (c) is 30 ppm or less.

2. The process of claim 1, wherein the undissolved phosphorous acid is removed by filtration.

3. The process of claim 1, wherein the undissolved phosphorous acid is removed by centrifugation.

4. The process of claim 1, wherein the acid content of the organophosphite following step (c) is 10 ppm or less.

5. The process of claim 1, wherein the acid content of the organophosphite following step (c) is 5 ppm or less.

6. The process of claim 1, further comprising (d) concentrating the organophosphite in hydrocarbon solution; (e) combining the concentrated organophosphite in hydrocarbon solution with an anti-solvent; and (f) collecting the resulting solids.

7. The process of claim 6, further comprising (g) storing the resulting solids for at least 30 days, wherein the stored resulting solids comprise 25 ppm or less phosphorous acid after 30 days.

8. The process of claim 6, wherein the organophosphite in hydrocarbon solution is concentrated to a residual hydrocarbon content of 50% by weight or less.

9. The process of claim 6, wherein the anti-solvent is added to the concentrated organophosphite in hydrocarbon solution.

10. The process of claim 6, wherein the anti-solvent is isopropanol or t-butanol.

11. The process of claim 6, wherein from 0.05 to 13 acid-neutralizing equivalents per 100 moles organophosphite of an acid-scavenger is added at or after step (f), wherein the acid content of the organophosphite following step (f) is 30 ppm or less.

12. The process of claim 1, further comprising providing the organophosphite to a hydroformylation process.

13. The process of claim 1, wherein the solid organophosphite compound comprising phosphorous acid has been stored for at least 30 days.

14. The process of claim 1, wherein the organophosphite compound comprises at least one of the following:
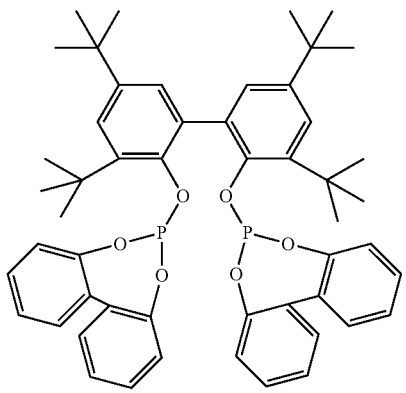
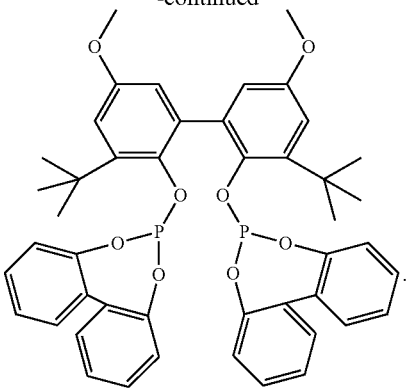
15. The process of claim 1, wherein the solid organophosphite compound is dissolved in the hydrocarbon solvent in the absence of water and free amine.
* * * * *